United States Patent
McFadden

(10) Patent No.: US 6,489,787 B1
(45) Date of Patent: Dec. 3, 2002

(54) GAS DETECTION CIRCUIT

(75) Inventor: Edward F. McFadden, Charlottesville, VA (US)

(73) Assignee: Bacharach, Inc., New Kensington, PA (US)

(*) Notice: Subject to any disclaimer, the term of this patent is extended or adjusted under 35 U.S.C. 154(b) by 103 days.

(21) Appl. No.: 09/689,990

(22) Filed: Oct. 13, 2000

Related U.S. Application Data

(60) Provisional application No. 60/175,624, filed on Jan. 11, 2000.

(51) Int. Cl.[7] ............... G01R 17/10; G01R 27/28; G01R 27/08
(52) U.S. Cl. ............... 324/725; 324/656; 324/657; 324/706
(58) Field of Search ............... 324/725, 706, 324/651, 656, 680, 657, 703, 612; 702/24; 73/23.2, 25.01, 31.05; 422/90, 94, 96, 98

(56) References Cited

U.S. PATENT DOCUMENTS

| | | | | |
|---|---|---|---|---|
| 3,678,489 A | | 7/1972 | Scherban et al. | 340/237 R |
| 4,013,943 A | | 3/1977 | Chou et al. | 324/33 |
| 4,164,699 A | | 8/1979 | Timoshenko et al. | 323/75 A |
| 4,166,380 A | | 9/1979 | Batz | 73/23 |
| 4,305,724 A | * | 12/1981 | Micko | 324/71 R |
| 4,315,210 A | * | 2/1982 | Michel et al. | 324/612 |
| 4,375,353 A | | 3/1983 | Nicholas et al. | 431/13 |
| 4,404,843 A | | 9/1983 | Johnson et al. | 73/49.2 |
| 4,476,706 A | * | 10/1984 | Hadden et al. | 73/1.07 |
| 4,507,558 A | | 3/1985 | Bonne | 250/345 |
| 4,736,193 A | | 4/1988 | Slocum et al. | 340/522 |
| 4,740,777 A | | 4/1988 | Slocum et al. | 340/522 |
| 4,818,977 A | * | 4/1989 | Alexander | 324/703 |
| 4,835,522 A | | 5/1989 | Andrejasich et al. | 340/521 |
| 4,847,783 A | * | 7/1989 | Grace et al. | 702/24 |
| 4,958,076 A | | 9/1990 | Bonne et al. | 250/343 |
| 5,055,269 A | * | 10/1991 | Palumbo et al. | 324/706 |
| 5,117,676 A | | 6/1992 | Chang | 73/40.5 A |
| 5,159,277 A | * | 10/1992 | Mount | 324/706 |
| 5,189,362 A | * | 2/1993 | Dobie | 324/706 |
| 5,305,231 A | * | 4/1994 | Coppler et al. | 702/24 |
| 5,416,724 A | | 5/1995 | Savic | 364/509 |
| 5,528,225 A | * | 6/1996 | Sakai et al. | 422/98 |
| 5,563,578 A | | 10/1996 | Isenstein | 340/521 |
| 5,586,050 A | | 12/1996 | Makel et al. | 364/509 |
| 5,650,943 A | | 7/1997 | Powell et al. | 364/550 |
| 5,918,260 A | * | 6/1999 | Newman et al. | 422/96 |
| 5,991,707 A | * | 11/1999 | Searles et al. | 324/71.3 |
| 6,373,056 B1 | * | 4/2002 | Johnson et al. | 250/339.13 |

\* cited by examiner

*Primary Examiner*—Michael Sherry
*Assistant Examiner*—Jermele Hollington
(74) *Attorney, Agent, or Firm*—Webb Ziesenheim Logsdon Orkin & Hanson, P.C.

(57) ABSTRACT

A circuit capable of detecting natural gas at a wide range of concentrations is disclosed. The gas detection circuit includes a catalytic Wheatstone bridge circuit and an analyzing Wheatstone bridge circuit. A circuit for detecting natural gas, which includes placing a device containing the circuit described above in an area in which the air has a potential of containing natural gas, and monitoring the output signal for indications of the presence of natural gas is also disclosed.

19 Claims, 4 Drawing Sheets

GAS DETECTION CIRCUIT

CROSS-REFERENCE TO RELATED APPLICATION

This application claims the benefit of earlier filed U.S. Provisional Patent Application Ser. No. 60/175,624 filed Jan. 11, 2000, entitled "Gas Detection Circuit."

BACKGROUND OF THE INVENTION

1. Field of the Invention

The present invention relates to a method for detecting gas leaks. More particularly, the present invention is directed to an electronic circuit that can detect natural gas at any level.

2. Description of the Prior Art

In the natural gas distribution industry, there is a need to detect and test for natural gas at several concentrations. Natural gas detection at part per million concentrations is required to locate leaks in piping and around equipment connections. Higher levels of natural gas can lead to explosive reaction. The concentration of natural gas can build to such levels over time if a leak occurs in an enclosed area. For this reason, it is necessary to measure natural gas in enclosed areas where leakage can occur and concentrations may build to levels capable of explosive reaction in order to provide warning of an explosive hazard. Natural gas concentrations beyond the explosive range can be caused by leakage into small closed volumes, such as around a buried gas pipe or in regulator pits. Natural gas concentration readings in these instances may be used to precisely locate leaks, thereby reducing the cost to repair lines by limiting the excavation necessary to expose the leaking section.

The preferred natural gas detection method can vary depending on the concentration of natural gas anticipated. For example, if part per million or explosive concentrations of natural gas are anticipated, a catalytic detector can be used. For natural gas concentrations beyond the explosive range, a detector based on thermal conductivity methods of measurement may be used.

Examples of catalytic gas detectors are described in U.S. Pat. No. 3,678,489 to Scherban et al.; U.S. Pat. No. 4,164,699 to Timoshenko et al.; U.S. Pat. No. 4,375,353 to Nicholas et al.; and U.S. Pat. No. 5,563,578 to Isenstein. U.S. Pat. No. 5,586,050 to Makel et al. discloses the use of a catalytic gas detector from Det-Tronics, Minneapolis, Minnesota. Examples of Det-Tronics detectors are Det-Tronics Model 226530-01 and CGS Detector.

Catalytic detectors typically react to a combustible gas which may come from a variety of sources with oxygen from the surrounding air. The reaction between combustible vapors and air is promoted by the catalytic material on the surface of one of two elements. The elements are electrically and thermally matched, temperature sensitive, resistive elements. The combustion reaction on the catalytically-coated element releases heat, raising the temperature of that element and, therefore, its resistance, with respect to the matching element which is not catalytically coated. This resistive imbalance is measured in a Wheatstone bridge circuit with the signal output derived being connected to additional electrical components to perform a variety of functions. U.S. Pat. No. 5,055,269 to Palumbo et al. discloses this type of detector.

Another type of gas leak detector used to detect high concentration gas leaks is based on an acoustic detection system where microphones are used to "listen" for the sound of gas leaking from a pipe, fitting, or valve. Such acoustic methods are disclosed in U.S. Pat. No. 5,117,676 to Chang; U.S. Pat. No. 5,416,724 to Savic; and U.S. Pat. No. 5,650,943 to Powell et al. These methods have a drawback in that in order for a leak to be audible, it must be significant. Therefore, early detection is not provided.

An expensive method developed for natural gas detection is based on the use of infrared absorption. U.S. Pat. No. 4,507,558 to Bonne and U.S. Pat. No. 4,958,076 to Bonne et al. disclose methods of selective natural gas detection utilizing absorption of infrared radiation. These methods are limited primarily to low concentration detection.

Still another method for detecting natural gas is described in U.S. Pat. No. 4,013,943 to Chou et al. This method involves a solid state electrolytic cell sensor that causes the dissociation of the gas into charged species, such as ions and complex ions. This method also utilizes a heater, which can be dangerous and is limited as to how low the detection limit for natural gas can be.

There remains a need for a safe and inexpensive means for detecting natural gas at any concentration.

SUMMARY OF THE INVENTION

The present invention is directed to a unique circuit capable of detecting natural gas at a wide range of concentrations. The gas detection circuit includes a catalytic Wheatstone bridge circuit and an analyzing Wheatstone bridge circuit. The catalytic Wheatstone bridge circuit includes an active element and a reference element on a first half of the catalytic Wheatstone bridge circuit and a first fixed resistor and a second fixed resistor on a second half of the catalytic Wheatstone bridge circuit. The analyzing Wheatstone bridge circuit includes the active element and the reference element in series, acting as a single element in series with a third fixed resistor on a first half of the analyzing Wheatstone bridge circuit. A second half of the analyzing Wheatstone bridge circuit includes a fourth fixed resistor and a fifth fixed resistor, which balance the first half of the analyzing Wheatstone bridge circuit.

The catalytic Wheatstone bridge circuit and analyzing Wheatstone bridge circuit are powered by maintaining a fixed voltage difference across the respective Wheatstone bridge circuits. An output signal is taken from the midpoint of the half bridge at the juncture of the active element and the reference element for comparison to the voltage at the midpoint of the two matched balancing resistors, which are the first fixed resistor and the second fixed resistor. The intensity of the signal is proportional to the concentration of natural gas.

The present invention is also directed to a method of detecting natural gas. The method includes placing a device containing the circuit described above in an area in which the air has a potential of containing natural gas and monitoring the output signal for indications of the presence of natural gas.

These and other advantages of the present invention will be clarified in the description of the preferred embodiment taken together with the attached drawings in which like reference numerals represent like elements throughout.

DETAILED DESCRIPTION OF THE PREFERRED EMBODIMENTS

Figure 1:
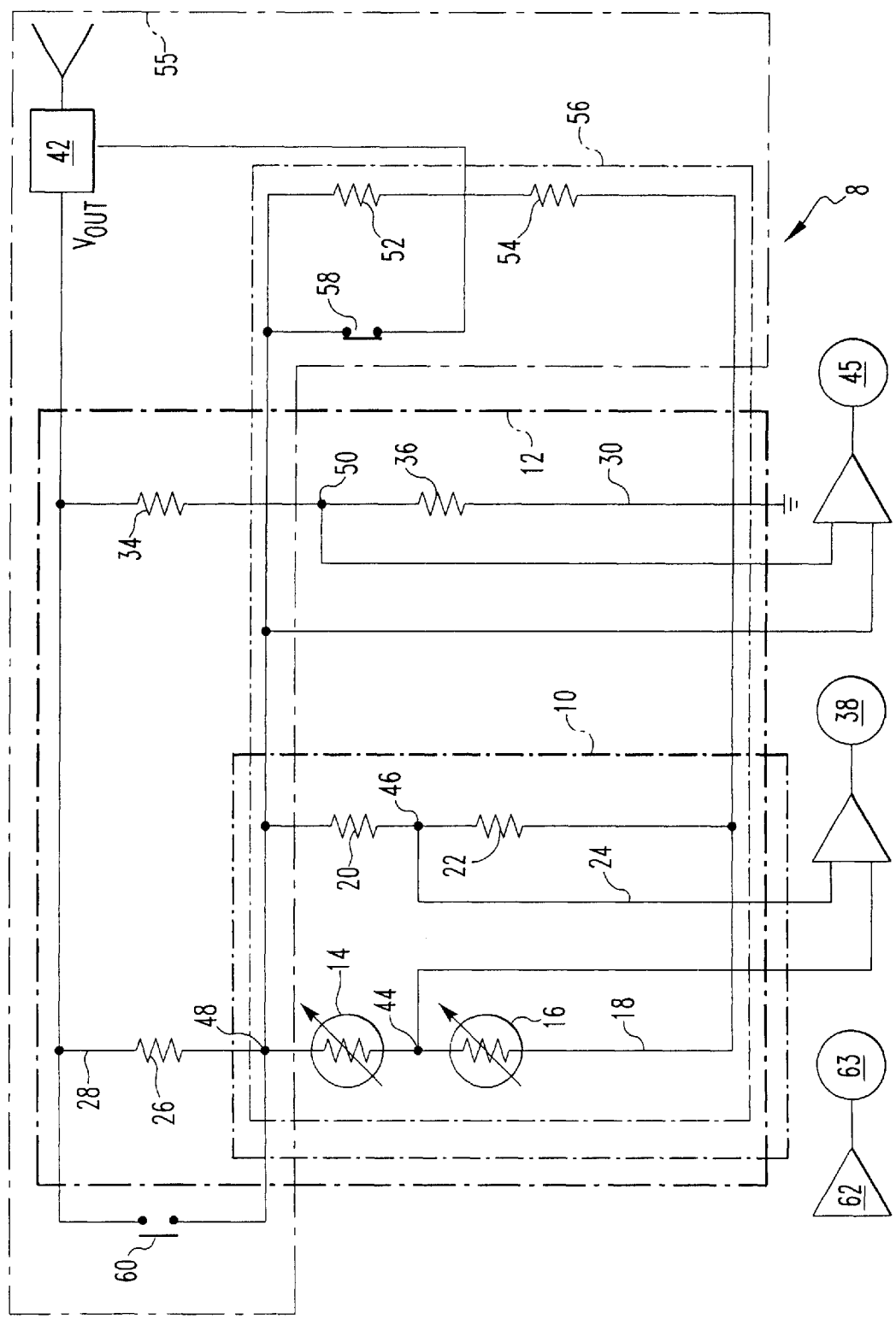
FIG. 1 is a schematic diagram of the gas detection circuit of the present invention.

Referring to FIG. 1, a gas detection circuit 8 of the present invention includes a catalytic Wheatstone bridge circuit 10 and an analyzing Wheatstone bridge circuit 12. The catalytic Wheatstone bridge circuit 10 includes an active element 14 and a reference element 16 on a first half 18 of the catalytic Wheatstone bridge circuit 10 and a first fixed resistor 20 and a second fixed resistor 22 on a second half 24 of the catalytic Wheatstone bridge circuit 10. The analyzing Wheatstone bridge circuit 12 includes the active element 14 and the reference element 16 in series, acting as a single element in series with a third fixed resistor 26 on a first half 28 of the analyzing Wheatstone bridge circuit 12. A second half 30 of the analyzing Wheatstone bridge circuit 12 includes a fourth fixed resistor 34 and a fifth fixed resistor 36, which balance the first half 28 of the analyzing Wheatstone bridge circuit 12.

The catalytic Wheatstone bridge circuit 10 is powered by a fixed voltage regulator 42, which maintains a fixed voltage difference across catalytic Wheatstone bridge circuit 10. A first output signal 38 is taken from the midpoint of a first half 18 of catalytic Wheatstone bridge circuit 10 at a first juncture 44 of active element 14 and reference element 16 for comparison to the voltage at the midpoint of a second half 24 of catalytic Wheatstone bridge circuit 10 taken from the midpoint of the two matched balancing resistors, which is a second juncture 46 located between first fixed resistor 20 and second fixed resistor 22.

In the high percentage gas concentration range, analyzing Wheatstone bridge circuit 12, which acts as a thermal conductivity Wheatstone bridge circuit, is used. Fixed voltage regulator 42 provides power, which is regulated voltage controlled to maintain a fixed voltage difference across the matched elements of analyzing Wheatstone bridge circuit 12. The voltage is applied to third fixed resistor 26 connected in series with active element 14 and reference element 16 and to series connected fourth fixed resistor 34 and fifth fixed resistor 36. Fourth fixed resistor 34 and fifth fixed resistor 36 are connected in parallel with third fixed resistor 26, active element 14, and reference element 16. Third fixed resistor 26 becomes a current-sensing resistor in conjunction with the fixed voltage maintained across sensing elements, active element 14, and reference element 16, allowing determination of the resistance of active element 14 and reference element 16. A second signal output 45 is taken from a third juncture 48 located between third fixed resistor 26 and active element 14 and from a fourth juncture 50 located between fourth fixed resistor 34 and fifth fixed resistor 36.

The thermal conductivity detector, analyzing Wheatstone bridge circuit 12, operates on the well-recognized principle that a heated element exposed to gasses with different thermal conductivities will vary in resistance with the relative concentrations of the gas mixture to which it is exposed. By measuring the resistance of the two matched elements in comparison to the series fixed resistor, a signal may be derived which is proportional to the concentration of methane (natural gas is 90% or higher methane) in air over the full range of concentration from 0 to 100% by volume.

The power supplied to the catalytic elements, active element 14 and reference element 16, when connected in the thermal conductivity bridge circuit, analyzing Wheatstone bridge circuit 12, is much lower than that used for catalytic measurements. The power requirement is determined by a regulator and switching circuit 55, which is external to analyzing Wheatstone bridge circuit 12 and catalytic Wheatstone bridge circuit 10. Regulator and switching circuit 55 includes the fixed voltage regulator 42, which controls voltage $V_{out}$, a voltage sensing circuit 56, a first range control switch 58, and a second range control switch 60. Voltage sensing circuit 56 includes a sixth fixed resistor 52 and a seventh fixed resistor 54 connected in parallel with the catalytic detector elements, active element 14 and reference element 16. First range control switch 58 is externally controlled and capable of shorting out sixth fixed resistor 52 in the high gas concentration range. This increases the sensed voltage applied to catalytic Wheatstone bridge circuit 10 when the sensed voltage is reduced by the ratio of the resistance of sixth fixed resistor 52 to the resistance of seventh fixed resistor 54. Second range control switch 60 controls selection of the point to which the voltage is applied, bypassing third fixed resistor 26 for the catalytic Wheatstone bridge circuit 10, and including third fixed resistor 26 in the circuit for the thermal conductivity bridge circuit, analyzing Wheatstone bridge circuit 12. When sensing high concentrations of gas, above the lower explosive limit (LEL), the catalytic detector voltage is about one-half of the voltage supplied for catalytic operation. The change in detector voltage prevents the detector from catalytically-reacting methane, which requires a high operating voltage in comparison to most other hydrocarbon vapors for catalytic reaction.

The power supplied by fixed voltage regulator 42 maintains a fixed voltage across the catalytic detector elements, active element 14 and reference element 16, using current sensing third fixed resistor 26 to measure changes in resistance of the catalytic detector elements. This method of power control results in second output signal 45, which is much more linear than either voltage or current regulation of analyzing Wheatstone bridge circuit 12. However, voltage or current regulation of analyzing Wheatstone bridge circuit 12 could also be used within the scope of the present invention to provide a similar operation if suitable correction for linearity were made by other devices. In this mode of operation, reference element 16 and active element 14 are cooled by increasing concentrations of methane, lowering their resistance. The output signal 44 used to determine concentration is the total resistance (voltage) of elements 14 and 16 in series, providing an enhanced signal level for improved accuracy. Since elements 14 and 16 of the catalytic detector are temperature sensitive, and the current sensing resistor (third fixed resistor 26) is not, it is necessary to correct the offset (zero) using the temperature of the block in which the elements are mounted. The temperature is measured by thermocouple 62, which provides a temperature output signal 63. A microprocessor (not shown) is used to combine both output signals 38 and 45 with temperature output signal 63 to calculate temperature-adjusted output signals. It is possible to thermally match third fixed resistor 26 to the detector characteristics in order to eliminate the offset correction, however, this would result in a more expensive and complex detector assembly.

Another factor that can cause a serious error in the output readings is the variety of gasses present. For example, many gas distribution companies use a mixture of propane and air in place of, or in addition to, methane under high load conditions, which simplifies natural gas storage. Propane is lower in conductivity than air and can lead to erroneous readings in the high, thermal conductivity range.

The concept of the thermal conductivity analysis, as described above, is to reduce the catalyst temperature on the detector to below the temperature at which a methane/air reaction will occur. Measurement at such a temperature is possible since methane is the most stable hydrocarbon and the most difficult to react requiring a high catalyst temperature. Propane is more easily reacted by the catalyst, allowing reaction at a lower temperature or detection voltage. By operating the detector below the methane reaction temperature and monitoring the resistance of both detector elements, active (catalyzed) element 14 and reference (non-catalyzed) element 16 separately, it is possible to detect a difference in element temperature which would not exist if propane were not present. This first output signal 38 provides a fault indication, improving the reliability of the test method.

One embodiment of the gas detection circuit of the present invention uses a detector assembly part number 4P-100 from City Technology Ltd., Portsmouth, England, which includes both the active element 14 as well as balancing reference element 16 in a sealed assembly. The circuit, with appropriate choice of related elements, will work with any compensated, matched catalytic detector. Normal operating voltage for this detector, when operating in the catalytic detection mode, is 3.0 Volts. The electrical current is approximately 90 ma resulting in a resistance of 30 Ohms at this voltage. Elements first fixed resistor 20 and second fixed resistor 22 are fixed, metal film resistors reasonably matched to allow the output to be balanced by the electronic circuits (for example, 1% resistors). The resistors would usually be chosen to have as high a value as possible for reduced operating power, they must be of low enough value not to load the output device, in this case an operational amplifier. Voltage is regulated by a solid state circuit, which could be, for example, an operational amplifier driving a power transistor to control output voltage. Equally acceptable is an integrated circuit adjustable linear regulator, or a switching regulator circuit, for reduced power loss. The regulated voltage must pass through second range control switch 60, which, in the embodiment chosen, is a field effect transistor (FET) chosen for low on resistance. The voltage drop across second range control switch 60 is important because the greater the voltage drop, the less battery capacity will be recovered. A TN0602N3 low threshold transistor by Supertex, Inc. of Sunnyvale, California was chosen to achieve these characteristics.

For high-range operation, the FET is turned off (second range control switch 60 opened) so power flows through third fixed resistor 26, to active element 14 and reference element 16 and first fixed resistor 20, and second fixed resistor 22 to ground. Active element 14, reference element 16, first fixed resistor 20 and second fixed resistor 22 act as a single, temperature sensitive resistance matched by third fixed resistor 26 to form one-half of a Wheatstone bridge circuit. The balancing resistors in the bridge are fourth fixed resistor 34 and fifth fixed resistor 36. Third fixed resistor 26 is sized to match the resistance of the four elements, active element 14, reference element 16, first fixed resistor 20, and second fixed resistor 22, operating at a voltage nominally one-half of the voltage used for catalytic operation (1.5 Volts in this case). The resistance of the detector elements at the reduced voltage is approximately 20 Ohms, and third fixed resistor 26 was chosen to meet this value.

Not shown in the schematic is a circuit to null out the detector bridges to allow measurement on an analog-to-digital (A/D) converter with limited input range. This allows for the use of a less expensive device. The scheme used in this embodiment is a pulse width modulated signal from the microprocessor, which is fed to the reference input of an operational amplifier whose output is applied to the inputs of the signal amplifiers through a suitable resistor network. This scheme allows a variable offset which can be varied, by varying the pulse width at the startup of the instrument, until the bridge offset is within allowable limits, which allows proper operation of the A/D converter.

The detection circuit operates in two distinctly different modes: (1) a lower range mode going to but not exceeding 100% of the lower explosive limit (LEL) of methane or 5% by volume, depending on how the display is chosen and (2) a higher concentration range going to 100% by volume of methane starting at any concentration up to 5% by volume.

The lower range (1) operates on the catalytic detection method, which is well known in the art and uses standard design catalytic detectors readily available from a variety of sources. The higher concentration range (2) uses the basic thermal conductivity method of detection employing a novel method of using a standard catalytic detector as the sensing element. The range is selected automatically by the microprocessor. The higher range is less accurate at lower concentrations of natural gas than the lower range.

In the lower range, the catalytic detector is used with fixed resistors in a Wheatstone bridge configuration with a regulated voltage excitation. The outputs are caused as the catalytic element reacts with methane, increasing the temperature and resistance with respect to the reference element. The bridge circuit, as a result, becomes unbalanced, which provides an output that is linear with respect to the percentage of the LEL up to 100% of the LEL. This electrical signal may be applied to the input to an operational amplifier whose output feeds into an A/D converter, which is subsequently sent in digital format to the microprocessor. Normally, the output would go to a display device, such as a liquid crystal display (LCD), and to alarm indicators, such as a light emitting diode (LED), and/or audible devices, relays, etc. Information on detector gain and alarm levels is stored in microprocessor memory.

The high range would be selected automatically by the microprocessor when the low range has been exceeded. Again, the output signal is applied as an input to an operational amplifier and then to an A/D converter and the microprocessor input. The information is again applied to a digital display as a convenience. A bar graph may be used to track the concentration levels and also to retain the highest reading. Alarms are not usually used in the high gas range.

Figure 2A:
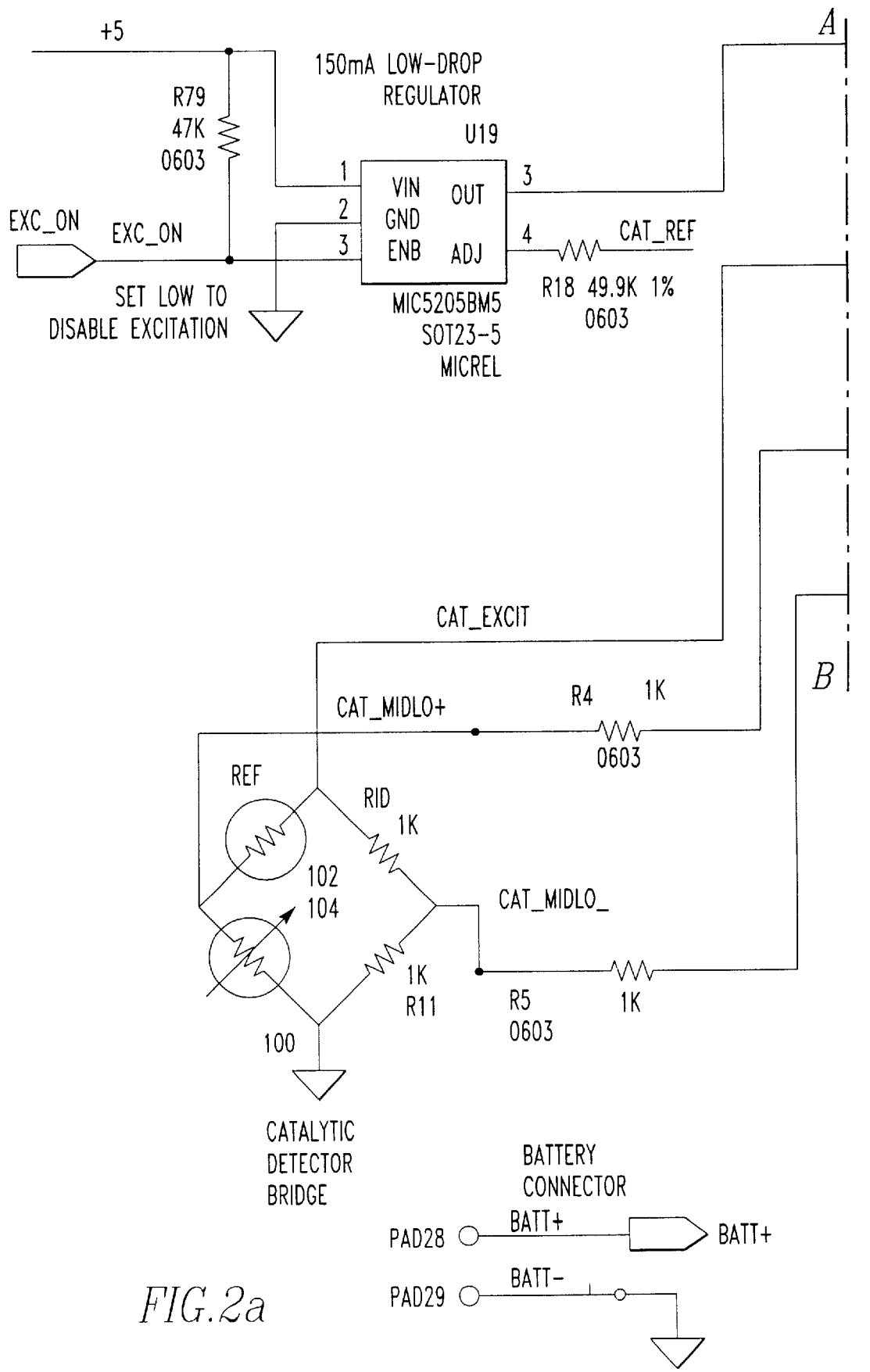
FIGS. 2a, 2b, and 2c are a schematic diagram of an embodiment of the gas detection circuit of the present invention.
Figure 2B:
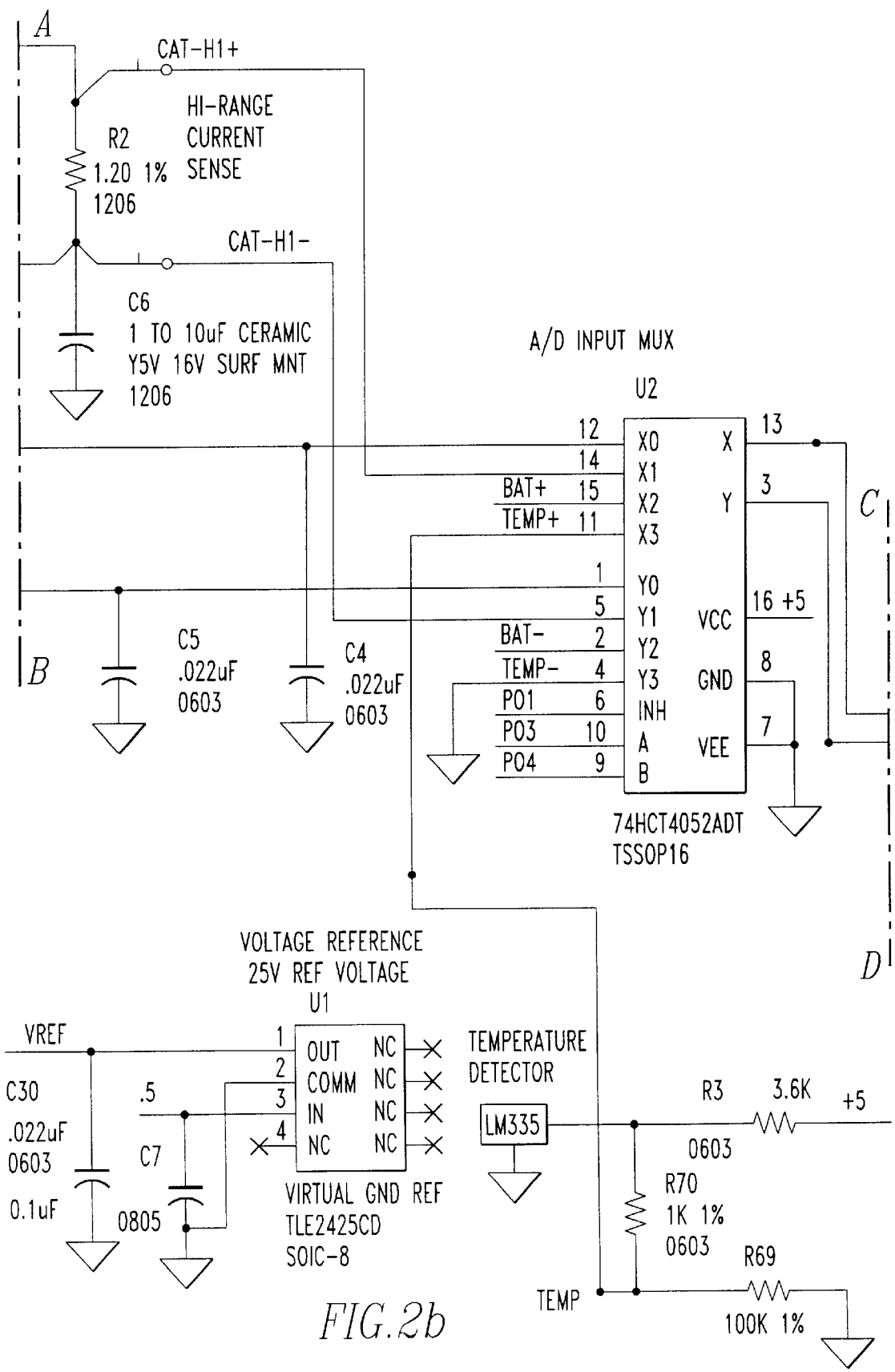
Figure 2C:
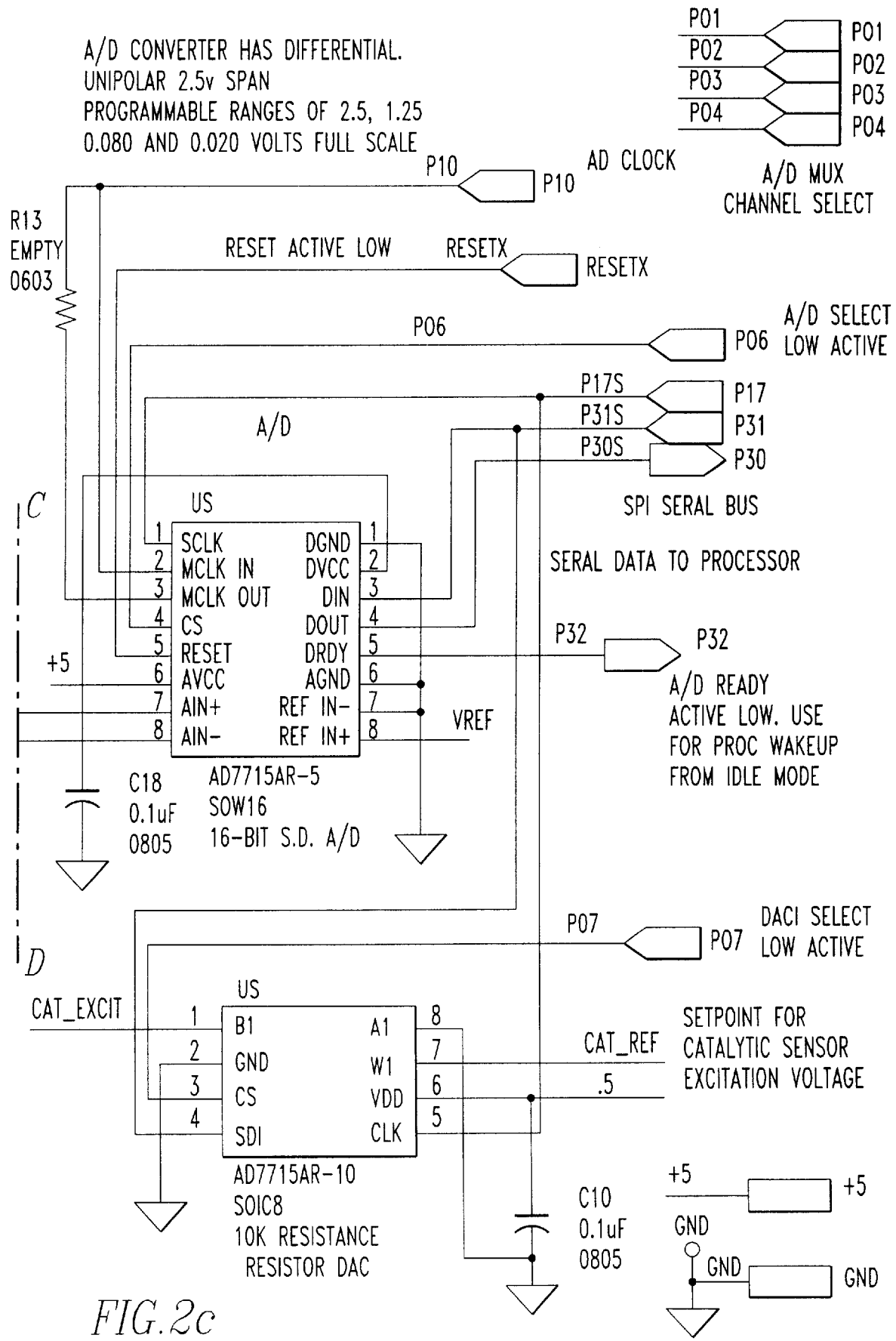

The following is a description of a multi-range methane detector using the gas detection circuit of the present invention and its operation. Referring to FIG. 2, a standard catalytic detector bridge 100, with an active element 104 and a reference element 102, is used for detection, and a first balancing resistor R10 and a second balancing resistor R11 are balancing resistors in a standard Wheatstone bridge configuration. Power is supplied as an excitation voltage CAT_EXCIT, via a low drop out adjustable voltage regulator U19. Adjustable voltage regulator U19 is programmed via a resistor digital-to-analog converter (DAC) U5 using an analog output signal CAT_REF. Resistor DAC U5 is controlled by a first digital input P17S from first microprocessor port P17 and a second digital input P31S from second microprocessor port P31, which provides a command to control the value of the resistance of resistor DAC U5. The resistance of resistor DAC U5 provides an analog output signal CAT_REF.

The excitation current to catalytic detector bridge 100 passes through a current sensing resistor R2. Catalytic detector bridge 100 provides a first bridge signal CAT_MIDLO+ and a second bridge signal CAT_MIDLO−, which are sent to a digital multiplexer U2. Digital multiplexer U2 sequentially sends the input signals to an A/D CONVERTER U4, which digitizes the analog signals and transfers them to a third microprocessor port P30 as a third input signal P30S. Alternatively, the third input signal could be transmitted to a microcomputer, minicomputer, or a computer. Digital multiplexer U2 also receives a first input signal CAT_HI+, which is the input to current sensing resistor R2 and second input signal CAT_HI−, which is the output from current sensing resistor R2. Digital multiplexer U2 also receives a voltage signal TEMP, which is proportional to the temperature of catalytic detector bridge 100 and is referenced to ground.

In operation, a voltage is applied to catalytic detector bridge 100, which is sufficient to cause a reaction between air and methane gas, releasing heat, which raises the temperature of active element 104 of catalytic detector bridge 100, resulting in an unbalance between first input signal CAT_MIDLO+ and second input signal CAT_MIDLO−, which is proportional to the concentration of methane at low-volume concentrations. Above the LEL, the determination of methane concentration based on first input signal CAT_HI+ and second input signal CAT_HI− may become unreliable. Exposure above the LEL may damage the detector.

When the LEL is reached, excitation voltage CAT_EXCITE is reduced by changing analog output signal CAT_REF. The excitation voltage CAT_EXCITE is reduced sufficiently in that catalytic detection bridge 100 will no longer react to methane and air. In this situation, digital multiplexer U2 sends first input signal CAT_HI+ and second input signal CAT_HI− from current sensing resistor R2 to A/D CONVERTER U4, rather than first bridge signal CAT_MIDLO+ and second bridge signal CAT_MIDLO− from catalytic detector bridge 100. The current sensing resistor circuit allows a direct measurement of the resistance of the sensor bridge circuit, which changes in direct proportion to the concentration of methane, since methane has a higher thermal conductivity than air.

In order to use the change in resistance of the detector bridge to measure high concentrations of methane, an initial resistance must be determined and stored by a microprocessor at start up, using air without methane as a basis. A similar activity is performed on the low-range methane reading. When the detector switches to the high range, this stored value is used as a baseline or zero value. The high range detection relies on the fact that the higher thermal conductivity of methane will cool the detector, lowering the resistance with increasing concentration, since the detector element is constructed of a material, normally platinum, which has a significant temperature coefficient of resistance. This results in an error with changes in ambient temperature unless compensated. The use of a device providing a predictable voltage output versus temperature allows an initial value to be determined at startup and later compared by a microprocessor to real-time values to correct the inherent change in catalytic detector resistance with ambient temperature.

The present invention is also directed to a method of detecting natural gas. The method includes placing a device containing the gas detection circuit of the present invention in an area in which the air has a potential of containing natural gas and monitoring the output signal for indications of the presence of natural gas. Alternatively, the method includes using a hand-held device, wherein the gas detection circuit of the present invention is used for determining the amount and location of natural gas leaks. In the latter method, the hand-held device is moved along or next to tanks, pipes, or other structures, which contain natural gas. If natural gas should be leaking from the structures, the hand-held detection device will signal the presence of natural gas. More specifically, when either method is used, active element 14 is exposed to the air in the area to be sampled. As described above, first output signal 38, second output signal 44, and temperature output signal 63 are generated and transmitted for monitoring. First output signal 38, second output signal 44, and temperature output signal 63 can be transmitted by hard wiring, radio transmission, or fiber-optic link through the use of appropriate transmitter/receiver modules known in the art.

First output signal 38, second output signal 44, and temperature output signal 63 are received by a computer or microprocessor system incorporating an A/D and a digital display or by a radio receiver.

Based on first output signal 38, second output signal 44, and temperature output signal 63, the concentration of natural gas is determined by comparing the output signal to that of a known concentration of natural gas (a standard) by the use of a computer, microcomputer, or microprocessor of the appropriate circuitry. The circuit can then display the natural gas concentration on a digital or analog display, transmit the value to another computer, activate a visual or audio alarm, display the concentration on a display, such as a bar graph display, or produce an audio signal whose frequency or "click" rate is proportional to the gas concentration.

Generally, one standard natural gas mixture is used to calibrate analyzing Wheatstone bridge circuit 12 and another is used to calibrate the catalytic Wheatstone bridge circuit 10.

The invention has been described with reference to the preferred embodiments. Obvious modifications and alterations will occur to others upon reading and understanding the preceding detailed description. It is intended that the invention be construed as including all such modifications and alterations insofar as they come within the scope of appended claims or the equivalents thereof.

I claim:
1. A natural gas detection circuit comprised of:
a first Wheatstone bridge circuit comprised of:
an active element;
a reference element, said active element and said reference element aligned in series on a first half of said first Wheatstone bridge circuit;
a first fixed resistor; and
a second fixed resistor, the first fixed resistor and the second fixed resistor aligned in series on a second half of said first Wheatstone bridge circuit, said first half of said first Wheatstone bridge circuit being aligned in parallel with said second half of said first Wheatstone bridge circuit; and
a second Wheatstone bridge circuit comprised of:
said active element;
said reference element;
a third fixed resistor, said active element, said reference element, and said third fixed resistor aligned in series on a first half of said second Wheatstone bridge circuit;
a fourth fixed resistor;
a fifth fixed resistor, said fourth fixed resistor and said fifth fixed resistor aligned in series on a second half of said second Wheatstone bridge circuit, said first half of said second Wheatstone bridge circuit being aligned in parallel with said second half of said second Wheatstone bridge circuit; and a fixed voltage regulator, which provides power to said gas detection circuit, the fixed voltage regulator maintaining a fixed voltage difference across said first Wheatstone bridge circuit and said second Wheatstone bridge circuit.

2. The natural gas detection circuit as claimed in claim 1 further comprising a regulator and switching circuit comprised of:
   said fixed voltage regulator; and
   a voltage sensing circuit comprised of:
      a sixth fixed resistor;
      a seventh fixed resistor, said sixth fixed resistor and said seventh fixed resistor aligned in series, and together being aligned in parallel with said first Wheatstone bridge circuit;
   a first range control switch capable of shorting out the sixth fixed resistor; and
   a second range control switch capable of controlling selection of the point to which the voltage is supplied between said first Wheatstone bridge circuit and said second Wheatstone bridge circuit.

3. The natural gas detection circuit as claimed in claim 2, further comprising a first output signal taken from said first half of said first Wheatstone bridge circuit at a point between said active element and said reference element for comparison to the voltage of said second half of said first Wheatstone bridge circuit, taken from a point between said first fixed resistor and said second fixed resistor and a second output signal taken from a point located between said third fixed resistor and said active element on said first half of said second Wheatstone bridge circuit for comparison to the voltage of said second half of said first Wheatstone bridge circuit, taken from a point between said fourth fixed resistor and said fifth fixed resistor.

4. The natural gas detection circuit as claimed in claim 3, further comprising a thermocouple capable of providing a temperature output signal.

5. The natural gas detection circuit as claimed in claim 4, wherein a microprocessor is used to combine said first output signal, said second output signal, and said temperature output signal and calculates a temperature adjusted output signal.

6. The natural gas detection circuit as claimed in claim 4, wherein a digital multiplexer receives and sequentially sends said first output signal said second output signal, and said temperature output signal to an analog-to-digital converter, wherein said first output signal, said second output signal, and said temperature output signal are digitized.

7. The natural gas detection circuit as claimed in claim 6, wherein said analog-to-digital converter transmits said digitized signals to a microprocessor, microcomputer, minicomputer, or computer.

8. The natural gas detection circuit as claimed in claim 7, wherein said transmission is accomplished by using hard wiring, radio transmission, or fiber-optic link.

9. The natural gas detection circuit as claimed in claim 8, wherein said transmission is received by a computer or microprocessor system incorporating an analog-to-digital converter and output devices selected from the list consisting of a digital display, liquid crystal display, audible alarm indicators, visual alarm indicators, a bar graph, and an audible click proportional to natural gas concentration.

10. The natural gas detection circuit as claimed in claim 2, wherein said second range control switch is closed when the natural gas concentration in air is at or below the lower explosive limit or 5% by volume of natural gas, directing a voltage to be applied across said first Wheatstone bridge circuit and said second range control switch is open when the natural gas concentration in air is above the lower explosive limit or 5% by volume of natural gas, directing the voltage to be applied across said second Wheatstone bridge circuit.

11. The natural gas detection circuit as claimed in claim 10, wherein said voltage applied when said second range control switch is closed is about one-half of the voltage applied when said second range control switch is open.

12. A hand-held natural gas detection device that includes a natural gas detection circuit comprised of:
   a first Wheatstone bridge circuit comprised of:
      an active element;
      a reference element, said active element and said reference element aligned in series on a first half of said first Wheatstone bridge circuit;
      a first fixed resistor; and
      a second fixed resistor, the first fixed resistor and the second fixed resistor aligned in series on a second half of said first Wheatstone bridge circuit, said first half of said first Wheatstone bridge circuit being aligned in parallel with said second half of said first Wheatstone bridge circuit;
   a second Wheatstone bridge circuit comprised of:
      said active element;
      said reference element;
      a third fixed resistor, said active element, said reference element, and said third fixed resistor aligned in series on a first half of said second Wheatstone bridge circuit;
      a fourth fixed resistor;
      a fifth fixed resistor, said fourth fixed resistor and said fifth fixed resistor aligned in series on a second half of said second Wheatstone bridge circuit, said first half of said second Wheatstone bridge circuit being aligned in parallel with said second half of said second Wheatstone bridge circuit;
   a fixed voltage regulator, which provides power to said gas detection circuit, the fixed voltage regulator maintaining a fixed voltage difference across said first Wheatstone bridge circuit and said second Wheatstone bridge circuit;
   a voltage sensing circuit comprised of:
      a sixth fixed resistor;
      a seventh fixed resistor, said sixth fixed resistor and said seventh fixed resistor aligned in series, and together being aligned in parallel with said first Wheatstone bridge circuit;
   a first range control switch capable of shorting out the sixth fixed resistor;
   a second range control switch capable of controlling selection of the point to which the voltage is supplied between said first Wheatstone bridge circuit and said second Wheatstone bridge circuit;
   a first output signal taken from said first half of said first Wheatstone bridge circuit at a point between said active element and said reference element for comparison to the voltage of said second half of said first Wheatstone bridge circuit, taken from a point between said first fixed resistor and said second fixed resistor and a second output signal taken from a point located between said third fixed resistor and said active element on said first half of said second Wheatstone bridge circuit for comparison to the voltage of said second half of said first Wheatstone bridge circuit, taken from a point between said fourth fixed resistor and said fifth fixed resistor; and a thermocouple capable of providing a temperature output signal, wherein a digital multiplexer receives and sequentially sends said first output signal, said second output signal, and said temperature output signal to an analog-to-digital converter, wherein said first output signal, said second output signal, and said temperature output signal are digitized; said analog-to-digital converter transmits said digitized signals to a microprocessor, microcomputer, minicomputer, or computer; said transmission is accomplished by using hard wiring, radio transmission, or fiber-optic link; and said transmission is received by a computer or microprocessor system incorporating an analog-to-digital converter and output devices selected from the list consisting of a digital display, liquid crystal display, audible alarm indicators, visual alarm indicators, a bar graph, and an audible click proportional to natural gas concentration.

13. A method of detecting natural gas comprising the steps of:
   placing a device in an area in which the air has a potential of containing natural gas, said device containing a circuit comprised of:
      a first Wheatstone bridge circuit comprised of:
         an active element;
         a reference element, said active element and said reference element aligned in series on a first half of said first Wheatstone bridge circuit;
         a first fixed resistor; and
         a second fixed resistor, the first fixed resistor and the second fixed resistor aligned in series on a second half of said first Wheatstone bridge circuit, said first half of said first Wheatstone bridge circuit being aligned in parallel with said second half of said first Wheatstone bridge circuit;
      a second Wheatstone bridge circuit comprised of:
         said active element;
         said reference element;
         a third fixed resistor, said active element, said reference element, and said third fixed resistor aligned in series on a first half of said second Wheatstone bridge circuit;
         a fourth fixed resistor; and
         a fifth fixed resistor, said fourth fixed resistor and said fifth fixed resistor aligned in series on a second half of said second Wheatstone bridge circuit, said first half of said second Wheatstone bridge circuit being aligned in parallel with said second half of said second Wheatstone bridge circuit;
      a fixed voltage regulator, which provides power to said gas detection circuit, said fixed voltage regulator maintaining a fixed voltage difference across said first Wheatstone bridge circuit and said second Wheatstone bridge circuit;
      a regulator and switching circuit comprised of:
         said fixed voltage regulator;
         a voltage sensing circuit comprised of:
            a sixth fixed resistor; and
            a seventh fixed resistor, said sixth fixed resistor and said seventh fixed resistor aligned in series, and together being aligned in parallel with said first Wheatstone bridge circuit;
      a first range control switch, capable of shorting out the sixth fixed resistor;
         a second range control switch, capable of controlling selection of the point to which the voltage is supplied between said first Wheatstone bridge circuit and said second Wheatstone bridge circuit;
         a first output signal taken from said first half of said first Wheatstone bridge circuit, at a point between said active element and said reference element, for comparison to the voltage of said second half of said first Wheatstone bridge circuit, taken from a point between said first fixed resistor and the second fixed resistor; and
         a second output signal taken from a point located between the third fixed resistor and said active element on said first half of said second Wheatstone bridge circuit, for comparison to the voltage of said second half of said first Wheatstone bridge circuit, taken from a point between said fourth fixed resistor and said fifth fixed resistor; and
   monitoring said first output signal and said second output signal for indications of the presence of natural gas.

14. The method of detecting natural gas as claimed in claim 13, wherein said gas detection circuit further comprises a thermocouple capable of providing a temperature output signal.

15. The method of detecting natural gas as claimed in claim 14, further comprising the steps of combining said first output signal, said second output signal, and said thermocouple signal using a microprocessor and calculating temperature adjusted output signals.

16. The method of detecting natural gas as claimed in claim 15, further comprising the steps of receiving said temperature adjusted output signals by a digital multiplexer, sequentially sending said temperature adjusted output signals to an analog-to-digital converter and digitizing said temperature adjusted output signals.

17. The method of detecting natural gas as claimed in claim 16, further comprising the step of transmitting said digitized signals from said analog-to-digital converter to a microprocessor, microcomputer, minicomputer, or computer.

18. The method of detecting natural gas as claimed in claim 17, wherein said transmission is accomplished by using hard wiring, radio transmission, or fiber-optic link.

19. The method of detecting natural gas as claimed in claim 18, further comprising the step of receiving said transmission by a computer or microprocessor system incorporating an analog-to-digital converter and output devices selected from the list consisting of a digital display, liquid crystal display, audible alarm indicators, visual alarm indicators, a bar graph, and an audible click proportional to natural gas concentration.

* * * * *